(12) United States Patent
Moeskops et al.

(10) Patent No.: US 10,265,799 B2
(45) Date of Patent: Apr. 23, 2019

(54) HAIR CUTTING DEVICE

(71) Applicant: KONINKLIJKE PHILIPS N.V., Eindhoven (NL)

(72) Inventors: Bastiaan Wilhelmus Maria Moeskops, Eindhoven (NL); Calina Ciuhu, Eindhoven (NL); Rudolf Maria Jozef Voncken, Eindhoven (NL); Klaas Hilverda, Eindhoven (NL); Geert Veenstra, Eindhoven (NL); Willem Auke Westerhof, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 594 days.

(21) Appl. No.: 14/773,522

(22) PCT Filed: Mar. 11, 2014

(86) PCT No.: PCT/EP2014/054616
§ 371 (c)(1),
(2) Date: Sep. 8, 2015

(87) PCT Pub. No.: WO2014/139968
PCT Pub. Date: Sep. 18, 2014

(65) Prior Publication Data
US 2016/0016256 A1    Jan. 21, 2016

(30) Foreign Application Priority Data

Mar. 11, 2013  (EP) .................................... 13158508

(51) Int. Cl.
*B23K 26/064* (2014.01)
*A61B 18/20* (2006.01)
*A61B 18/00* (2006.01)

(52) U.S. Cl.
CPC .......... *B23K 26/064* (2015.10); *A61B 18/203* (2013.01); *A61B 2018/00476* (2013.01); *A61B 2018/00601* (2013.01)

(58) Field of Classification Search
CPC ..... B23K 26/064; A61B 18/203; A61B 18/20; A61B 2018/00476; A61B 2018/00601
(Continued)

(56) References Cited

U.S. PATENT DOCUMENTS 5,182,857 A * 2/1993 Simon .................. A61B 18/203
132/118
5,993,440 A   11/1999 Ghassemi
(Continued)

FOREIGN PATENT DOCUMENTS

| JP | 2009028271 A | 2/2009 |
| JP | 2009034236 A | 2/2009 |

(Continued)

*Primary Examiner* — Boniface Nganga (57) ABSTRACT

The present application relates to a device for cutting hair comprising a skin contacting face (3) that is placed against a surface of the skin (6) of a user during use. The device also has an optical system configured to direct a cutting laser beam (8) across a cutting zone (5) parallel to and spaced from said skin contacting face to cut hairs extending into the cutting zone. Also provided is a laser positioning mechanism which is arranged so that, during use of the device, the distance (H1) between said cutting laser beam and said skin contacting face is changed to maintain a predetermined distance between the cutting laser beam and the surface of the skin of a user.

15 Claims, 7 Drawing Sheets

(58) Field of Classification Search
USPC .............. 606/9, 13, 19; 30/34.05, 140, 32
See application file for complete search history.

(56) References Cited

U.S. PATENT DOCUMENTS

| | | |
|---|---|---|
| 6,825,445 B2 | 5/2004 | Shalev |
| 9,295,518 B2 | 3/2016 | Verhagen |
| 2006/0200114 A1* | 9/2006 | Ferren .................. A61B 18/203 606/9 |
| 2007/0255359 A1 | 11/2007 | Neev |
| 2008/0255548 A1* | 10/2008 | Van Hal ............... A61B 18/203 606/10 |
| 2011/0166560 A1* | 7/2011 | Kuo .................... A61B 18/203 606/9 |
| 2012/0283803 A1 | 11/2012 | Liu |

FOREIGN PATENT DOCUMENTS

| | | |
|---|---|---|
| WO | 1992016338 A1 | 10/1992 |
| WO | 0203876 A2 | 1/2002 |
| WO | 2006067721 A1 | 6/2006 |

\* cited by examiner

HAIR CUTTING DEVICE

This application is the U.S. National Phase application under 35 U.S.C. § 371 of International Application No. PCT/EP2014/054616, filed on March 11, 2014, which claims the benefit of European Application No. 13158508.5 filed on March 11, 2013. These applications are hereby incorporated by reference herein.

FIELD OF THE INVENTION

This invention relates to a device for cutting hair, in particular, a device for controlling the cutting height of a laser beam for cutting hair.

BACKGROUND OF THE INVENTION

It is known to use a laser beam to sever hair as an alternative to an arrangement of mechanical cutting blades. Hair exposed to a laser beam will absorb energy from that laser beam and the hair will either be severed by vaporisation or by laser induced optical breakdown and a resulting shockwave. A laser beam requires no moving parts and so the problem of cutting elements becoming worn or blunt is eliminated. Moreover, use of a laser beam to sever hair avoids skin irritation caused by the sharp edges of mechanical blades contacting the skin. It is known from WO1992/16,338 and U.S. Pat. No. 5,993,440 to provide a device including a laser diode and reflective elements that direct a laser beam across a cutting zone so that the beam is substantially parallel to and spaced from the surface of the user's skin during use. In this way, as the device is moved across the skin, hairs that enter the cutting zone are exposed to the laser beam and severed at the point of interaction between the laser beam and the hair.

Shaving performance is typically measured by two criteria—closeness of shave and irritation of the skin. The cutting height is the distance between the surface of the skin and the point at which hairs are cut. A good performing shaver should minimise the cutting height and therefore minimise the remaining hair length by cutting the hairs as close as possible to the skin. A good performing shaver should also minimise the variation in cutting height to attain substantially uniform remaining hair length. However, positioning a laser beam close to the skin may cause skin irritation if heat and energy from the laser is incident on the skin. It is necessary to protect the skin from a laser beam to avoid causing damage or irritation to the skin. In a different application, hair trimmers or groomers are used to trim hair to a constant length. In this case, although closeness may not be a major performance factor, uniformity of remaining hair length is desirable and minimising skin irritation remains an important consideration.

The skin surface of a user is not a flat and uniform environment. Skin, especially for example the face, typically has many contours, wrinkles and folds over which the shaver must be able to effectively move while maintaining a short and uniform cutting height. Moreover, it is known that when using a shaving device by pressing such a device against the skin, the skin will dome in the area of contact between the skin and the shaver and this can be further exaggerated when the device is moved across the skin.

Typically, to limit the effects of skin doming and protect the skin from the laser and limit irritation, a lamella is positioned between the laser beam and the skin to manipulate hair and limit contact between the skin and laser beam. A lamella is a generally planar member that is positioned between the cutting element (mechanical or optical) and the skin of a user during use, usually being in contact with the skin. A typical lamella has a plurality of apertures which allow hairs to protrude through and into the cutting area. However, use of a lamella on a shaving device can be detrimental to the closeness of cut as it increases the minimum attainable distance between the skin surface and the laser beam. Moreover, a lamella is typically provided with a plurality of apertures through which the hairs protrude as the lamella is moved over the skin. However, this arrangement means that not all hairs on the skin surface would be aligned with an aperture during a single pass and so not all hairs would be able to protrude through the lamella into the cutting zone, meaning that more passes over each area of skin are required. This is inconvenient and extra contact with the skin will increase rubbing and may increase the amount of skin irritation caused. Furthermore, use of a lamella can result in a build up of debris in the region of the laser beam, particularly hair off-cuts and dust generated by the cutting process. This debris can accumulate in the apertures of the lamella and in the vicinity of the laser beam and will reduce the hair-catching ability of the lamella and also the cutting efficiency of the laser beam.

It is known from WO2006/067721 to provide cutting heads of a mechanical shaver with flexible mounts such that as the mechanical cutting heads are moved across the surface of the skin their orientation changes in response to the contours and undulations of the skin surface. In particular, the cutting heads are sprung mounted about pivots so that they tilt backwards when pressure is applied to them and the springs act to push the cutting heads against the surface of the skin. In this way, as the shaver is moved over contours in the surface of the skin the cutting heads can move so that they are always flat against the skin surface and provide the most effective cutting action.

It is know from US2006/0200114 to provide a device for hair treatment that directs an optical beam in a direction towards a user's skin so that it severs hair on the user's skin. The device includes a lens that can alter the focal length of the optical beam and thereby alter the height at which hairs are severed. However, at least some of the energy of the optical beam will be absorbed by the user's skin and this may cause irritation or even injury.

SUMMARY OF THE INVENTION

It is an object of the invention to provide a device for cutting hair using a laser beam which substantially alleviates or overcomes the problems mentioned above.

According to the present invention, there is provided a device for cutting hair comprising a skin contacting face that is arranged to be placed against a surface of the skin of a user during use, an optical system configured to direct a cutting laser beam across a cutting zone parallel to and spaced from said skin contacting face to cut hairs extending into the cutting zone, and a laser positioning mechanism arranged so that, when the device is in use, the distance between said cutting laser beam and said skin contacting face is changed to maintain a predetermined distance between the cutting laser beam and the surface of the skin of a user.

Therefore, a uniform cutting height can be maintained and variations in skin height can be accommodated by moving the cutting laser beam. In this way, skin doming and other skin height variations, such as skin contours, can be accommodated without reducing the performance of the device in terms of cutting height or skin irritation. Skin irritation will be reduced because the cutting laser beam will move in response to changes in the height of the skin in the cutting zone and so will not go within the predetermined distance of the skin and cause undue irritation.

Furthermore, the laser positioning mechanism removes the need for a lamella. As the cutting laser beam is able to move to follow the changes in skin height caused by doming and other effects, there is no requirement to hold the skin flat while it is being shaved or trimmed. Removing the lamella will reduce the minimum attainable cutting height as there is no component disposed between the cutting laser beam and the skin of the user. Alternatively, the skin height following feature of the invention may permit a thinner, lightweight lamella with larger apertures which overcomes many of the problems associated with conventional lamellae.

The laser positioning mechanism may comprise a skin surface follower attached to the optical system, the skin surface follower being arranged so that, when the device is in use, the skin surface follower contacts a surface of the skin below the cutting laser beam such that the skin surface follower moves together with the optical system relative to the skin contacting face to change the distance between the cutting laser beam and said skin contacting face.

The skin surface follower will contact the skin and move the cutting laser beam in direct response to changes in the surface of the skin in the cutting zone. Therefore, a closed, passive system of accurate skin surface following can be realised.

The skin surface follower may be configured to contact a surface of the skin of a user in the vicinity of the cutting laser beam in the cutting zone when the device is in use.

Therefore, the height of the skin being followed by the laser positioning mechanism is the skin which is being shaved or trimmed at that point, resulting in the most accurate cutting height.

The laser positioning mechanism may comprise a frame which is moveably mounted within the device, said frame comprising said skin surface follower and said optical system which comprises a first reflective element positioned to reflect an incident laser beam across the cutting zone.

By mounting the optical system and skin surface follower on a moveable frame the movement resulting from the skin surface following will be imparted on the frame and optical system and therefore the cutting laser beam will also be moved to change the distance between the cutting laser beam and the skin contacting face. The frame provides a stable and rigid platform for mounting the optical components, which must remain in accurate alignment during movement to maintain the position of the cutting laser beam in the cutting zone.

The device may further comprise a spring element to bias said moveable frame in a direction towards the surface of a user's skin so that the skin surface follower remains in contact with the user's skin when the device is in use.

Therefore, the skin surface follower and the spring will act against each other so that changes in the height of the skin within the cutting zone are followed by the moveable frame and therefore the cutting laser beam. If the skin height in the cutting zone is increasing, the skin surface follower will push the moveable frame away from the skin, against the spring element. On the other hand, if the skin height in the cutting zone is decreasing, the spring will urge the moveable frame towards the skin so that the skin surface follower remains in contact with the surface of the skin and the pre-determined distance between the cutting laser beam and the skin is maintained.

In one embodiment, the skin surface follower may comprise an aperture and the cutting laser beam extends across the cutting zone and through the aperture.

Therefore, the skin surface follower can be positioned as close as possible to the cutting laser beam to provide the most accurate skin surface following, which allows the pre-determined minimum cutting height to be reduced further.

In another embodiment, the skin surface follower comprises a recess and the cutting laser beam extends across the cutting zone within the recess.

Therefore, no part of the skin surface follower will be disposed between the cutting laser beam and the surface of the user's skin and hair cutting in the vicinity of the skin surface follower is not impeded.

The skin surface follower may comprise a distal face that forms the first reflective element.

Therefore, there may be no need for an additional skin contacting component. Moreover, the reflective element is located to the side of the cutting zone so would not impede the interaction between the cutting laser beam and the hairs to be cut.

The laser positioning mechanism may comprise an electronic sensor arranged to detect the surface of the skin in the cutting zone during use and an actuator configured to move said laser positioning mechanism to maintain a predetermined distance between the cutting laser beam and the surface of the skin of a user when the device is in use.

In combination with the electronic sensor of the detector, the actuator is able to accurately adjust the position of the cutting laser beam in response to changes in skin height in the cutting zone, using a dynamic control system. Moreover, if the device includes an actuator then the distance between the surface of the skin and the cutting laser beam can be set to any value. Therefore, the device can be used for a trimming function, where the cutting height (distance between the cutting laser beam and the surface of the skin) may be controlled to attain a uniform remaining hair length and avoid skin irritation.

The laser positioning mechanism may comprise a frame which is moveably mounted within the device and on which is mounted the optical system, wherein the actuator is configured to move said frame to maintain a predetermined distance between the cutting laser beam and the surface of the skin of a user when the device is in use.

The frame connects the optical system to the actuator which allows the actuator to move the cutting laser beam and therefore change the distance between the cutting laser beam and the skin contacting face. The electronic sensor may also be mounted to the moveable frame, or it may alternatively be mounted to the device. The frame provides a stable and rigid platform for mounting the optical components, which must remain in accurate alignment during movement to maintain the position of the cutting laser beam in the cutting zone.

The optical system may include at least a first reflective element, configured to reflect an incident laser beam across said cutting zone, and wherein the laser positioning mechanism comprises an actuator configured to move a component of said optical system to adjust the distance between said cutting laser beam and said skin contacting face of the device.

Movement of a component of the optical system will provide simple and accurate adjustment of the position of the cutting laser beam in the cutting zone. Altering a reflection angle or position of a component can control the cutting height of the cutting laser beam without having to move a large assembly of components within the device. The actuator can be small, simple and lightweight.

The actuator may be configured to move said first reflective element either along a path of the incident laser beam or along a path of the cutting laser beam in the cutting zone.

The first reflective element has a reflective angle so moving the element along either of the cutting or incident laser beam paths will alter the point at which the incident laser beam is reflected and thereby alter the path of the reflected cutting laser beam in the cutting zone.

The optical system may comprise an additional reflective element which reflects a laser beam such that it is incident on said first reflective element, and wherein said actuator is configured to move said additional reflective element to adjust the path of the incident laser beam which is incident on said first reflective element and thereby adjust the distance between the cutting laser beam and the skin contacting face.

Movement of the additional reflective element will alter the path of the reflected cutting laser beam and thereby alter the distance between the cutting laser beam and the skin contacting face. Only a small and simple movement of a relatively lightweight reflective element is required, which means only a small and lightweight actuator is required for this embodiment.

The optical system may further comprise two reflective elements rotatably mounted on parallel axes, wherein said two reflective elements are configured to reflect a laser beam onto said first reflective element and said actuator is configured to rotate said two reflective elements to adjust the path of the incident laser beam which is incident on the first reflective element.

Use of a galvanometer mirror arrangement, as defined above, will allow the path of the incident laser beam which is incident on the first reflective element to be simply and accurately controlled.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which:

FIG. 1b shows a front view schematic diagram of the cutting end of the device of FIG. 1a.

FIGS. 3b, 3c and 3d show side view schematic diagrams of different embodiments of the device shown in FIG. 3a.

FIG. 4b shows a side view schematic diagram of the device of FIG. 4a.

DETAILED DESCRIPTION OF THE EMBODIMENTS

Figure 1A:
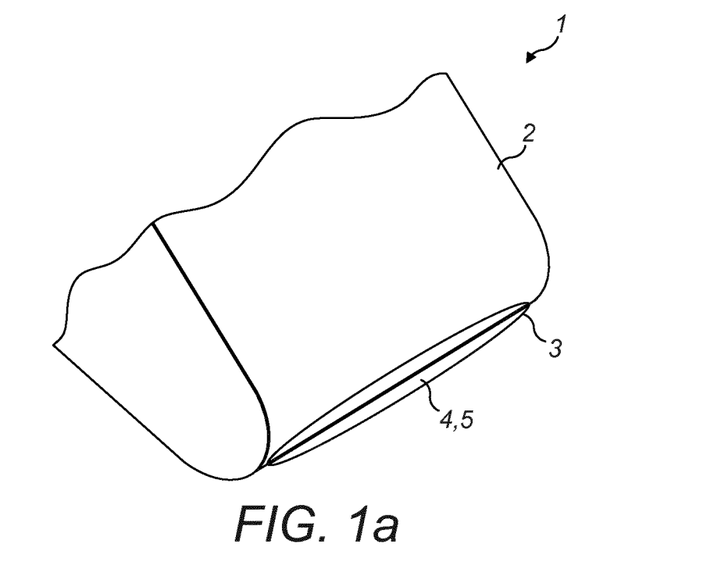
FIG. 1a shows a view of the cutting end of a device for cutting hair using a laser beam.
Figure 1B:
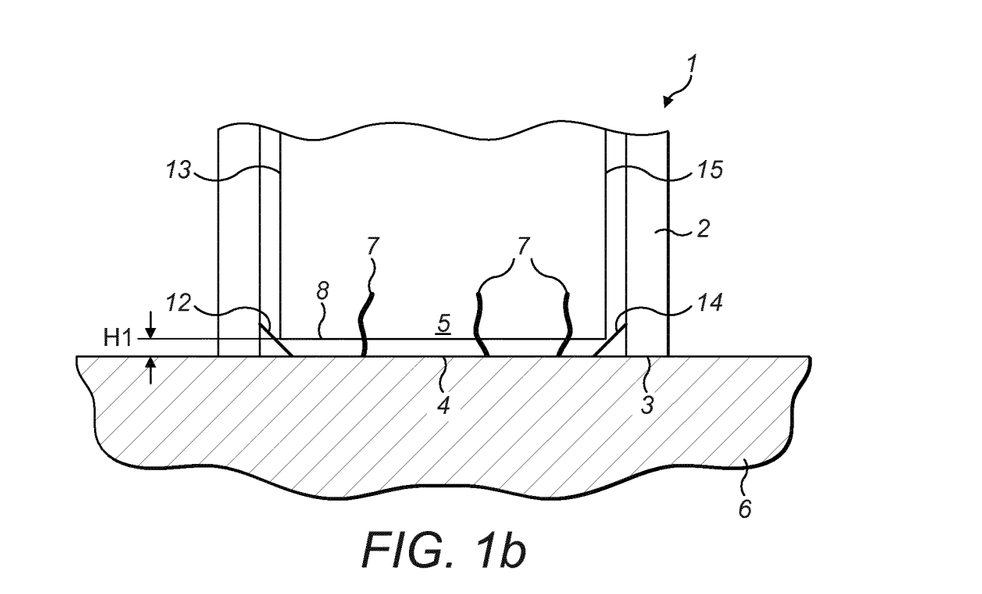

As shown in FIGS. 1a and 1b, which show the general features of the device of the invention, the device 1 comprises a main body 2 which includes a skin contacting face 3 having an opening 4. As shown in FIG. 1b, during use, the skin contacting face 3 of the main body 2 is placed against the skin 6 of a user and hairs 7 protrude into the opening 4 of the main body and into a cutting zone 5 defined therein. Within the opening 4 of the main body 2, the device 1 comprises an optical system which directs a cutting laser beam 8 across the cutting zone 5 so that the cutting laser beam 8 is parallel to and spaced from the skin contacting face 3 and opening 4 of the main body 2. In this way, when the skin contacting face 3 of the main body 2 is placed against the skin 6 of a user, the cutting laser beam 8 is substantially parallel to and spaced from the surface of the skin 6 of the user and provides a substantially uniform cutting height across the cutting zone 5. The distance between the surface of the skin 6 and the cutting laser beam 8 in the cutting zone 5, represented as distance H1 in FIG. 1b, would be the cutting height if the skin 6 in the cutting zone 5 were smooth and flat, without any doming.

Figure 2:
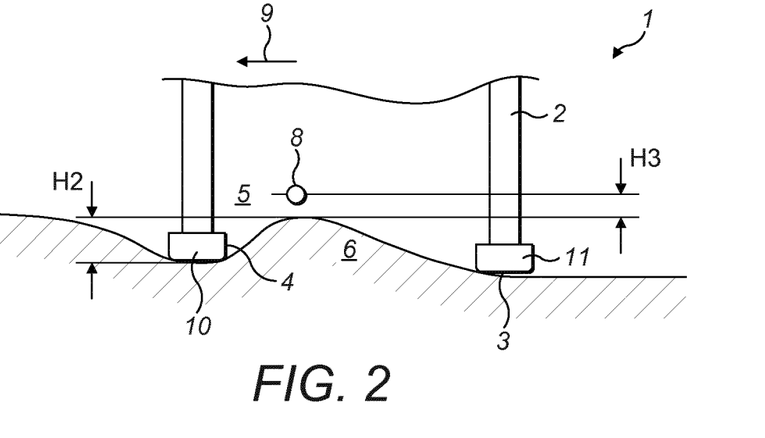
FIG. 2 shows a side view schematic diagram of the cutting end of the device of FIGS. 1a and 1b.

As explained previously, when a device 1 such as that shown in FIGS. 1a and 1b is placed against the skin 6 of a user the pressure applied by the user and movement of the device 1 across the skin 6 will cause deformation in the skin 6-doming. As shown in FIG. 2, which is a side view of the device of FIGS. 1a and 1b, when the device 1 is moved across the skin 6 in the direction of arrow 9 the skin 6 will dome into the cutting zone 5 causing the height H2 of the skin 6 within the cutting zone 5 to vary. The no-doming cutting height H1, as shown in FIG. 1b, is the distance between the skin contacting face 3 and the cutting laser beam 8. However, because the skin 6 domes into the cutting zone 5 this measurement is not an accurate reflection of the effective cutting height, which depends on the point at which the hairs are severed. The effective cutting height H3, as shown in FIG. 2, is the distance between the surface of the skin 6 and the cutting laser beam 8 at the point that the cutting laser beam 8 is closest to the skin 6, which will vary due to doming. The amount of doming will depend on the shape and configuration of the skin contacting face 3 and opening 4 of the device as well as the pressure applied during use. Furthermore, the speed and direction in which the device is moved across the skin 6 will also affect the size and shape of the skin doming. Moreover, doming will vary depending on the type of skin of the individual user and the part of the body being shaved. Therefore, it is very difficult to predict the amount of skin doming and set an appropriate fixed cutting height for a device for cutting hair.

To overcome this problem, the device is configured to move the position of the cutting laser beam 8 in a direction perpendicular to the longitudinal direction of the cutting laser beam 8 in the cutting zone 5, towards or away from the opening 4 and skin contacting face 3 of the main body 2, in response to changes in the height H2 of the skin 6 within the cutting zone 5. That is, the device is configured to maintain a consistent effective cutting height H3 in response to changes in the skin height H2 in the cutting zone 5 during use.

Also shown in FIG. 2, the skin contacting face 3 may be provided with a stretcher 10 which extends across the leading edge of the skin contacting face 3 of the main body 2 and acts to smoothly contact the skin 6 as the device 1 in moved across the skin surface in the direction of arrow 9. This will stretch out the skin 6 within the cutting zone 5 to smooth out any wrinkles or folds in the skin surface and help hairs on the skin surface to stand upright within the cutting zone 5, which is preferable for cutting the hairs with the cutting laser beam 8. The skin contacting face 3 of the main body 2 may also comprise a trailing low-friction part 11, extending across a trailing edge of the skin contacting face 3 of the main body 2, which also helps to hold the skin surface flat and stretch out any wrinkles or folds. It will be appreciated that the leading stretcher 10 and trailing low-friction part 10 may be replaced by two substantially identical stretchers to enable the device to work when being moved in both the direction of arrow 9 and the opposite direction. The stretchers 10, 11 may comprise a smooth, rounded surface so that they move smoothly across the skin surface without causing irritation. The stretchers 10, 11 may comprise a comb (not shown) to manipulate hairs as the device 1 is moved over the skin 6.

Movement of the cutting laser beam 8 in response to variations in skin height H2 in the cutting zone 5 will help to reduce, and may eliminate, the negative effects that doming causes for the quality and effectiveness of shaving. In particular, the device is able to move the cutting laser beam 8 to follow the variations in skin height H2 and thereby maintain a desired effective cutting height H3, while avoiding undue interaction between the cutting laser beam 8 and the skin 6. The cutting height of the cutting laser beam 8 in the cutting zone 5 can closely follow the height H2 of the skin 6, so that cutting performance, in terms of effective cutting height H3, uniformity of cut hair length and skin irritation, is greatly improved and a lamella may no longer be required.

It will be appreciated that moving the cutting laser beam 8 in response to changes in the skin height H2 in the cutting zone 5 will allow the device to maintain shaving performance regardless of the profile of the skin 6 within the cutting zone 6. The primary cause of variations in the skin profile is doming, as explained previously, but other factors also influence the skin profile and the movement of the cutting laser beam 8 provided by the invention will also account for these other variations. As described with reference to FIG. 2, one or more stretchers 10 and/or low-friction parts 11 may be provided and they will act to smooth out smaller skin features, with the movement of the laser beam acting to account for larger skin height variations caused by doming and contours in the skin.

The optical system of the device shown in FIG. 1b includes only those components that are positioned within the cutting end of the device 1. Other components that the device may comprise, which are not shown, may include a laser generator, such as a diode, and other optical components such as a collimating lens or filter. Other components necessary for the operation of the device may also be located within the main body 2, such as a battery or a connection to an external power cable. Moreover, the main body 2 of the device may also comprise a handle and any switches, buttons or other controls and displays necessary to operate the device. Any reflective elements described herein may comprise a mirror or a prism or any other optically reflective surface.

As shown in FIG. 1b, the optical system generally comprises a first reflective element 12 positioned on one side of the opening 4 and cutting zone 5, which is configured to reflect an incident laser beam 13 across the opening 4 at the end of the device 1, across the cutting zone 5, such that the cutting laser beam 8 follows a path which is substantially parallel to and spaced from the skin contacting face 3 and opening 4 of the device 1. On an opposite side of the cutting zone 5 to the first reflective element 12, a second reflective element 14 is positioned to reflect the cutting laser beam 8 away from the cutting zone 5, towards an energy dissipater (not shown) so that the 'used' laser beam 15 is dissipated and cannot interact with a part of the user or another part of the device. In the example shown in FIG. 1b, the incident laser beam 13 which is incident on the first reflective element 12 is perpendicular to the skin contacting face 3 of the main body 2 and the first reflective element 12 reflects the laser beam through 90 degrees such that it is parallel to the skin contacting face 3 of the main body 2. Similarly, the second reflective element 14 is configured to reflect the cutting laser beam 8 through 90 degrees and perpendicularly away from the cutting zone 5 back towards the main body 2 of the device 1. However, it will be appreciated that the first and second reflective elements 12, 14 may be orientated differently or have different reflective angles, depending on the position and orientation of other parts of the optical system, such as the laser beam generator and energy dissipater (not shown). Furthermore, it will be appreciated that the first and second reflective elements 12, 14 may not be located at a side of the cutting zone 5. They may alternatively be located anywhere within the cutting zone 5, depending on the position, orientation and configuration of the other components of the optical system. However, the cutting laser beam 8 within the cutting zone 5 should remain parallel to the skin contacting face 3 and opening 4 of the main body 2 so that the distance between the skin contacting face 3 and the cutting laser beam 8 is constant across the cutting zone 5.

Embodiments of the invention, all of which are configured to move the cutting height of the laser beam in response to changes in skin height within the cutting zone, are described hereinafter with reference to FIGS. 3a to 5c.

Figure 3A:
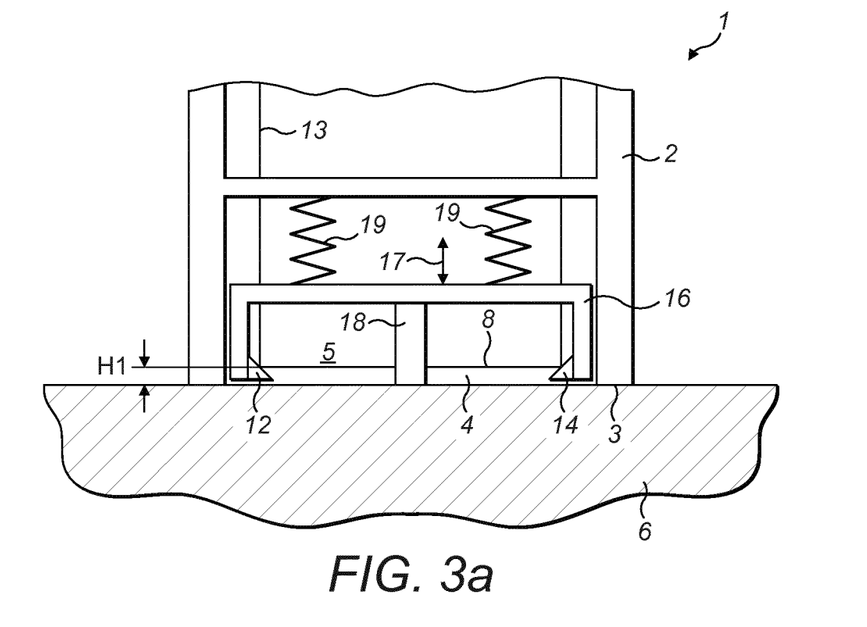
FIG. 3a shows a front view schematic diagram of the cutting end of a device for cutting hair, including a spring mounted moveable frame.
Figure 3B:
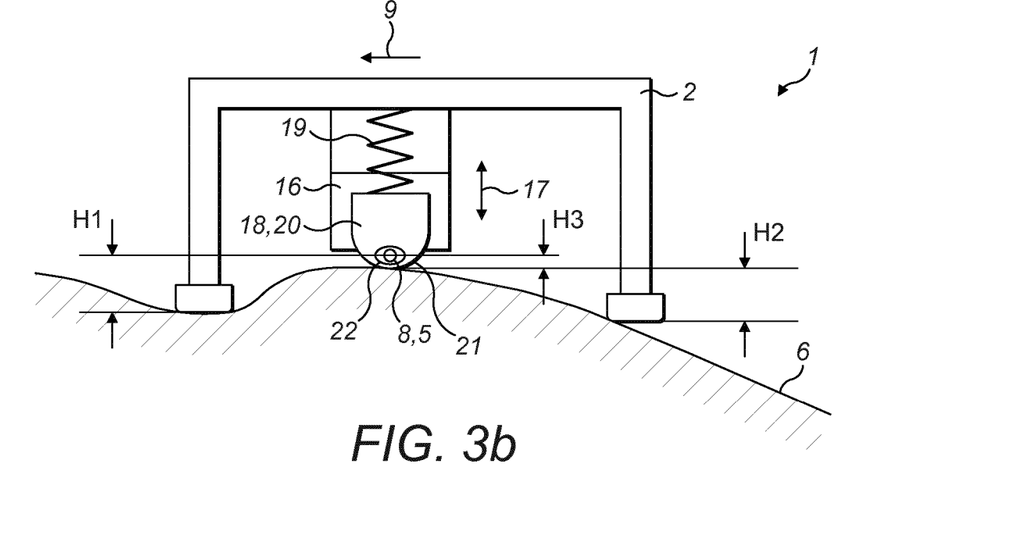

FIGS. 3a and 3b show an embodiment of a device 1 for cutting hair which includes a main body 2, as previously described with reference to FIGS. 1 and 2, which comprises an end opening 4 and a substantially planar skin contacting face 3 which is configured to contact the skin 6 during use of the device. Moreover, the skin contacting face 3 may be provided with leading and trailing edge stretchers 10, 11 to pull the skin 6 within the cutting zone 5 so that features of the skin 6 are smoothed out, as described with reference to FIG. 2.

As shown in FIG. 3a, the device 1 is also provided with a frame 16 that is moveably mounted within the main body 2 such that it is able to move towards and away from the skin contacting face 3 of the main body 2 in the direction of arrow 17. The components of the optical system are also mounted to the frame 16; in this example, the first and second reflective elements 12, 14 are positioned on the frame 16 to reflect an incident laser beam 13 across the cutting zone 5 to create a cutting laser beam 8, as previously explained. Movement of the frame 16 towards and away from the skin contacting face 3 of the main body 2 will vary the effective cutting height H3, as desired.

To achieve the desired movement of the cutting laser beam 8, in the direction of arrow 17, the frame 16 may be telescopically mounted within the main body 2 and that mounting may include linear slide bearings, rails or another connection that allows the frame 16 to slide relative to the main body 2. In this case, the frame 16 is mounted such that it can move in a direction 17 parallel to the incident laser beam 13 which is incident on the first reflective element 12. This movement is therefore perpendicular to the longitudinal direction of the cutting laser beam 8 within the cutting zone 5 and so the movement of the frame 16 will not effect the arrangement of the optical system, so that the incident laser beam 13 will still be reflected across the cutting zone 5 to form a cutting laser beam 8 which is parallel to the skin contacting face 3 of the device 1.

In the example shown in FIGS. 3a and 3b, the frame 16 is configured to move along linear rails which define a path 17 which is perpendicular to the plane of the opening 4 and skin contacting face 3 of the main body 2. That is, the frame 16 moves along the path of the incident laser beam 13 which is incident on the first reflective element 12. However, it will be appreciated that this movement may alternatively be at a non-perpendicular angle to the skin contacting face 3.

To enable the frame 16 to move in response to changes in the height H2 of the skin 6 within the cutting zone 5, the frame 16 also comprises at least one skin surface follower (18) configured to extend from the frame 16 towards the opening 4 of the device 1 so that, during use, it will contact the skin 6 of the user. Moreover, the device 1 is provided with at least one spring element 19 that acts between the main body 2 and the moveable frame 16 to urge the frame 16 away from the main body 2 towards the opening 4 and therefore, during use, the skin 6 of the user. In this way, the skin surface follower 18 remains in contact with the skin surface and, as the skin height H2 within the cutting zone 5 changes, the skin surface follower 18 is either pushed up by the contact with the skin 6, or down by the spring element 19 and the frame will also move in response to that variation. Therefore, the effective cutting height H3 of the cutting laser beam 8 will be maintained at a substantially constant value. To ensure that the effective cutting height H3 remains as constant as possible, the skin surface follower 18 is positioned on the frame 16 such that it is aligned with the cutting laser beam 8. In this way, the skin surface follower 18 is contacting the skin 6 at a point in line with the cutting laser beam 8, such that the skin height H2 being followed is that of the skin being shaved at that time and the effects of skin height H2 variations caused by doming are overcome.

FIGS. 3b to 3e show different embodiments of the skin surface follower 18 for the device described with reference to FIG. 3a.

In the example shown in FIG. 3b, the skin surface follower 18 comprises an arm member 20 which extends through the cutting zone 5 towards to the skin 6 of the user and has a rounded distal end 21 to ensure that the movement of the skin surface follower 18 over the skin 6 is smooth and does not cause undue irritation. In this embodiment of the skin surface follower 18, the arm member 20 is provided with an aperture 22 through which the cutting laser beam 8 passes as it moves across the cutting zone 5. The aperture 22 is positioned close to the distal end 21 of the arm member 20 which contacts the skin 6 and the aperture 22 extends through the arm member 20 so that the cutting laser beam 8 is not obstructed.

Figure 3C:
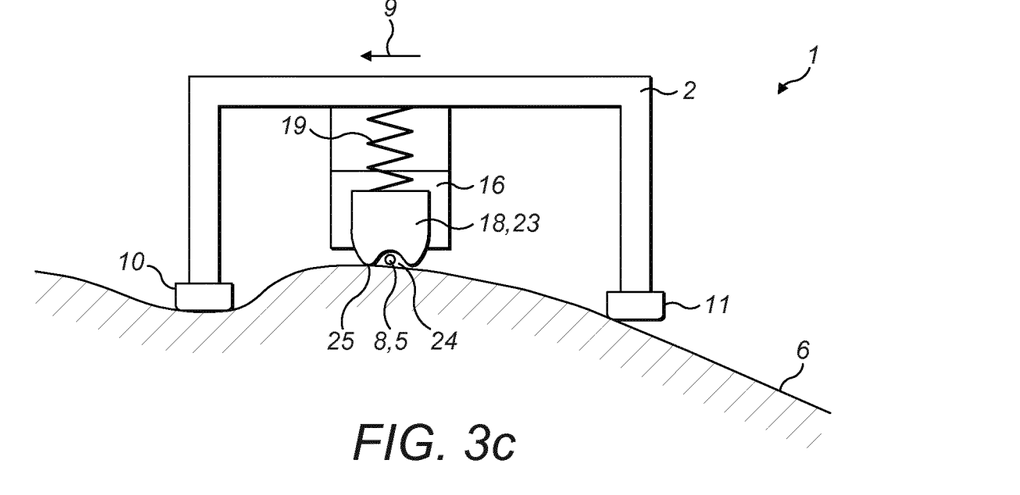

FIG. 3c shows a different embodiment of the skin surface follower 18. In particular, the skin surface follower 18 of this embodiment comprises an arm member 23 having a recess 24 through which the cutting laser beam 8 passes. The recess 24 extends to a distal end 25 of the skin surface follower such that no part of the arm member 23 is positioned between the cutting laser beam 8 and the skin 6 during use. Two edges of the recess 24, at the distal end 25 of the arm member 23, will contact the skin 6 during use while allowing the cutting laser beam 8 to extend between those edges, through the recess 24, so that it is not obstructed. In this way, the hair is not obstructed from the cutting laser beam 8 in the vicinity of the skin surface follower 18, while the skin following function of the arm member 23 is maintained as the device is moved over the skin 6 in the direction of arrow 9.

Figure 3D:
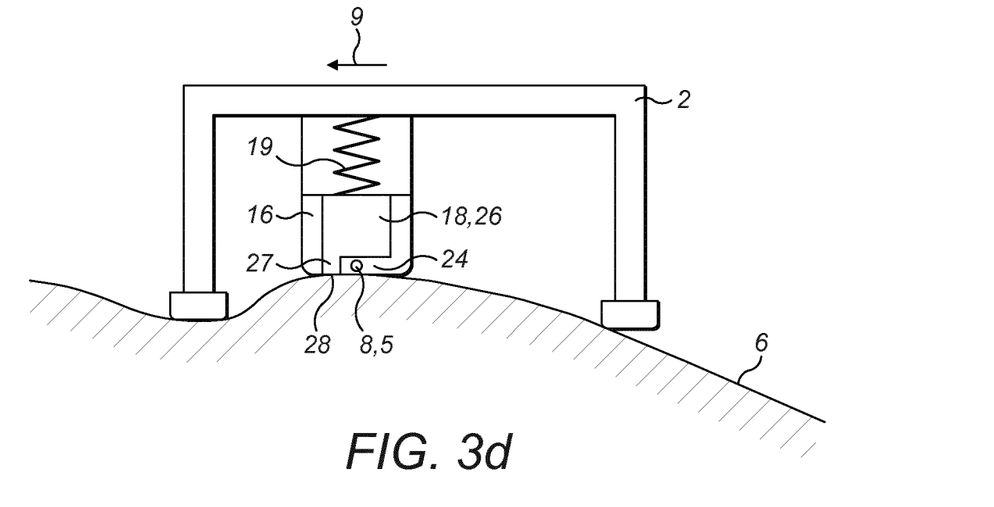

FIG. 3d shows another embodiment of the skin surface follower 18 as described with reference to FIG. 3a. In this embodiment, the skin surface follower 18 comprises an arm member 26 that only extends from the moveable frame 16 towards the skin 6 on one side of the cutting laser beam 8. This may be on the leading side of the cutting laser beam 8 or on the trailing side. This arrangement provides greater space around the cutting laser beam 8 in the vicinity of the skin surface follower 18, which allows hair to be more easily cut by the cutting laser beam 8 around the skin surface follower 18. The arm member 26 of the skin surface follower 18 comprises a recess 24 similar to that of the embodiment described with reference to FIG. 3c, however, the recess 24 of this embodiment is larger and extends such that only a skin contacting member 27 only extends past the cutting laser beam 8 on one side. That skin contacting member 27 may have a rounded and smooth distal end 28 which contacts the skin 6.

Figure 3E:
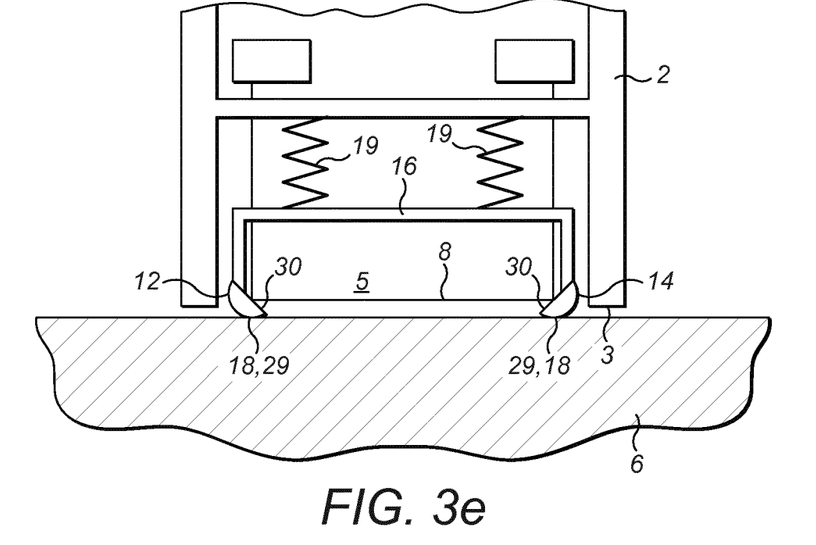
FIG. 3e shows a front view schematic diagram of the device for cutting hair, wherein the reflective elements comprise the skin detector.

FIG. 3e shows another embodiment in which the first and second reflective elements 12, 14 act also as the skin surface follower 18. In this case, the first and second reflective elements 12, 14 each comprise a smooth rounded distal end 29 as well as a reflective surface 30. It will be appreciated that the first reflective element 12 may comprise a skin following surface 29 whereas the second reflective element may not. Therefore, the reflective elements 12, 14, are able to satisfy the functions reflecting the cutting laser beam 8 across the cutting zone 5 and contacting the skin 6 to enable the skin height H2 to be followed by pushing the frame 16 against the spring 19. An advantage of this configuration is that the cutting laser beam 8 is totally exposed across the entire cutting zone 5 so hair cutting is not impeded by the skin surface follower 18.

It will appreciated that, although the embodiment of FIGS. 3a to 3d show a single skin surface follower 18 which extends from a central point of the moveable frame 16, the device may alternatively be provided with multiple skin surface followers. In particular, use of two skin surface followers will create a more uniform pressure between the skin and the frame, acting against the springs, and will place less twisting load on the linear slide mounts and reduce the likelihood of jamming and wear.

It will also be appreciated that a person skilled in the art would be able to select a spring 19, based on the exact size and configuration of the frame 16 and any sliding mounts, to achieve a uniform and appropriate spring force over the full travelling distance of the frame 16. In this way, the spring(s) 19 can apply a suitable and consistent force against the frame 16 and therefore the skin 6 during use. The force provided by the spring 19 should be sufficient to ensure adequate skin following without being so great that the skin surface follower 18 is overly pressed into the skin 6, which would cause more skin doming. The spring(s) 19 may be provided with a damper (not shown in the drawings) to damp the movement of the frame 16.

Figure 4A:
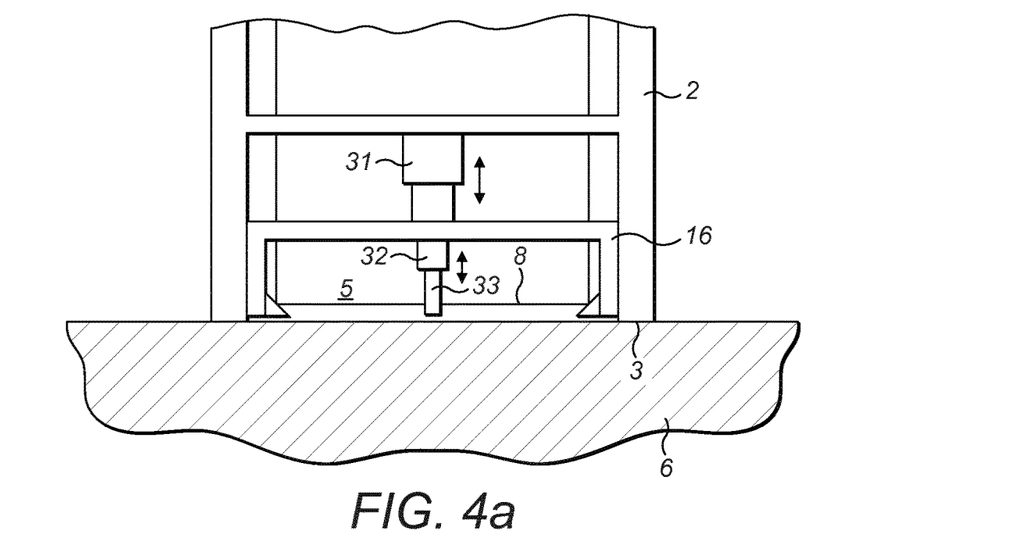
FIG. 4a shows a front view schematic diagram of a device for cutting hair which includes a sensor and an actuator.
Figure 4B:
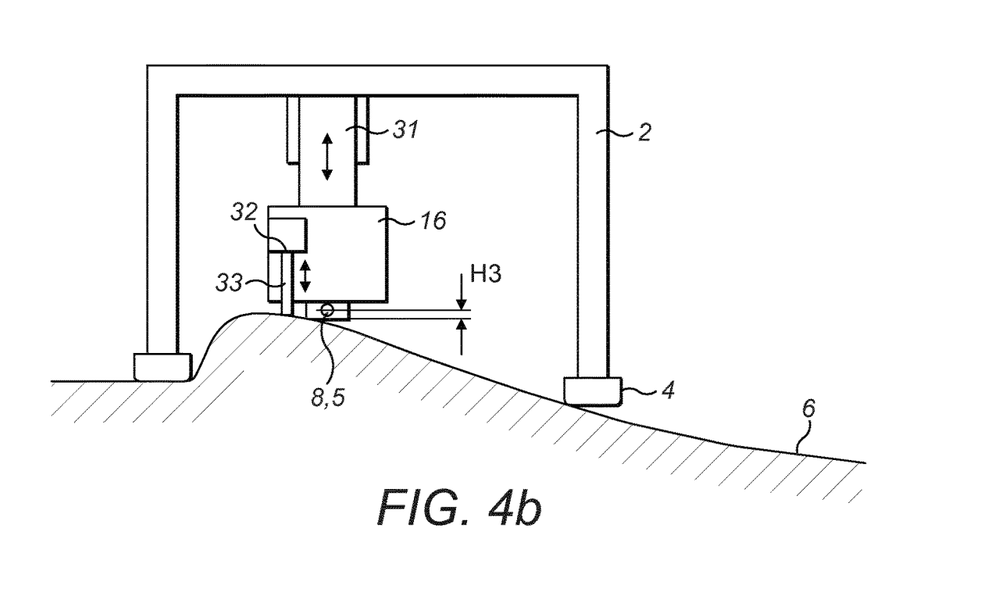

FIGS. 4a and 4b show a further embodiment of the device 1 for cutting hair, comprising a main body 2 with a skin contacting face 3 for contacting the user's skin 6 during use and a moveable frame 16 which is mounted in the main body 2, similar to the embodiments described with reference to FIGS. 3a to 3e. As shown in FIG. 4a, the moveable frame 16 of this embodiment is mounted on an actuator 31 which is configured to move the frame 16 and therefore the cutting laser beam 8 in a linear direction towards and away from the skin contacting face 3 of the main body 2 and therefore the skin 6 of the user during use. The actuator 31 may be an electronic actuator, for example a voice coil actuator, which moves the frame 16 in response to commands from a controller (not shown).

In this embodiment, the device 1 also includes a skin detector, in this case an electronic sensor 32 which determines the height H2 of the skin 6 within the cutting zone 5, in line with the cutting laser beam 8. That information is provided to the controller which controls the position of the actuator 31, which is configured to move the frame 16 and cutting laser beam 8 in response to the determined skin height H2. As shown in FIG. 4a, the sensor 32 may be an inductive sensor, such as a displacement potentiometer which has a sprung arm 33 which extends to contact the skin 6 in a similar fashion to the skin surface follower of the embodiments described with reference to FIGS. 3a to 3d. Alternatively, the skin detector may be an optical sensor, such as a confocal lens which uses optical measuring techniques and does not need to contact the skin to measure the distance between the surface of the skin a reference point on the device.

The skin detector sensor 32 may be mounted to the moveable frame 16, as shown in FIGS. 4a and 4b, and thereby move under the action of the actuator 31, in which case the controller is configured to move the actuator 31 to maintain a fixed determined measurement from the sensor 32, which equates to an appropriate effective cutting height H3. Alternatively, the sensor 32 may be mounted to the main body 2 of the device 1 (this configuration is not shown in drawings) and therefore the frame 16 moves independently of the sensor 32, within the device. In this case, the sensor 32 is configured to measure the skin height H2 in the cutting zone and the controller is configured to maintain a fixed determined difference between the measurement of the sensor 32 and the position of the actuator 31.

FIGS. 4a and 4b show a single, centrally located sensor 32 with a sprung arm 33 that extends towards the opening 4 of the device 1, close to the cutting laser beam 8. However, it will be appreciated that the device 1 may instead comprise multiple sensors positioned across the cutting zone 5 on either side of the cutting laser beam 8. Moreover, the device may include one or more actuators that control the position of the frame 16 within the device. For example, FIG. 4a shows a single, centrally located actuator 31 but this may be substituted with two spaced actuators acting synchronously.

Depending on the type of actuator used in this embodiment, the moveable frame 16 may be mounted on a linear sliding guide or rail within the main body 2 such that the frame 16 moves, under influence of the actuator 31, such that the cutting laser beam 8 in the frame 16 remains parallel to the skin contacting face 3 of the main body 2. The movement may be in direction which is perpendicular to the skin contacting face 3 of the main body 2 or it may be at an angle.

Alternatively, in an embodiment not shown in the drawings, a laser generator may be mounted to the cutting head frame which is rotatably mounted, such that the laser beam is moved away or towards the end opening and therefore the skin of the user. As the laser beam generator is also mounted to the rotatable frame the relative arrangement of the laser beam generator and the first reflective element is not affected by the rotation so the laser beam will still be reflected across the cutting zone such that it is parallel to the skin contacting face of the device. In this case, a skin surface follower and spring element arrangement similar to that described with reference to FIGS. 3a to 3e may be mounted to the rotatable frame so that the frame rotates to move the laser beam in response to changes in the height of the skin in the cutting zone. Alternatively, to reduce the weight of the rotatable frame, a sensor may be used in combination with an actuator to rotate the frame in response to changes in the height of the skin in the cutting zone, as detected by the sensor.

Figure 5A:
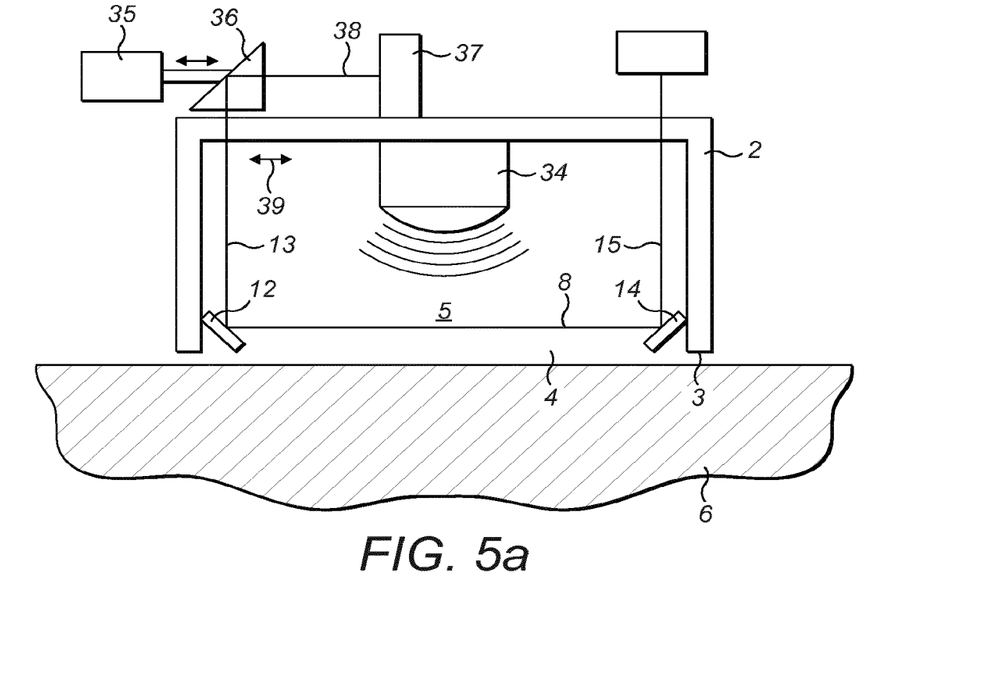
FIG. 5a shows a front view schematic diagram of a device for cutting hair having an optical system including an actuator.
Figure 5B:
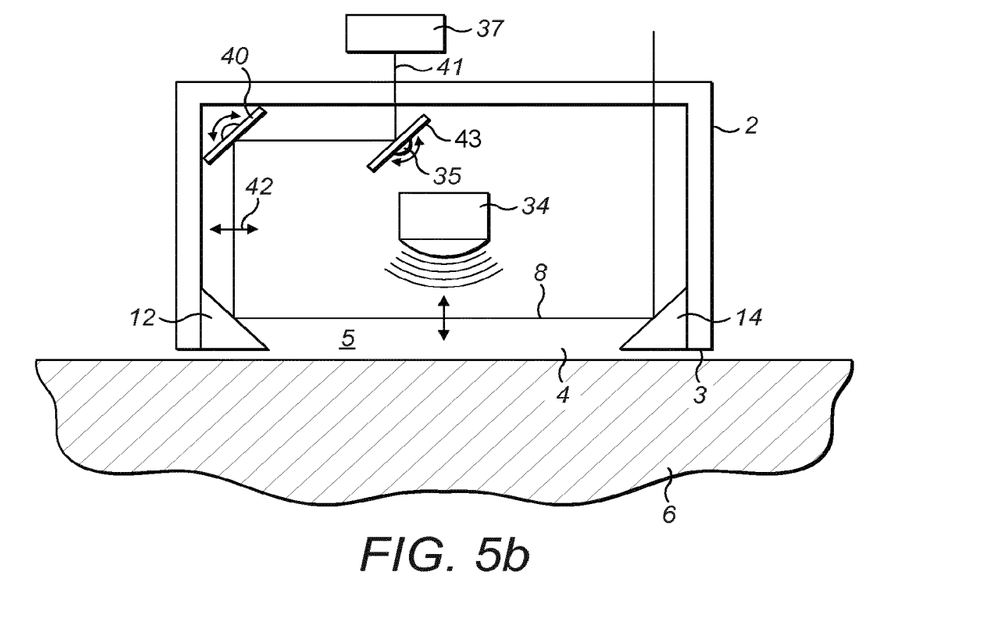
FIG. 5b shows a front view schematic diagram of another embodiment of the device for cutting hair having an optical system including an actuator.
Figure 5C:
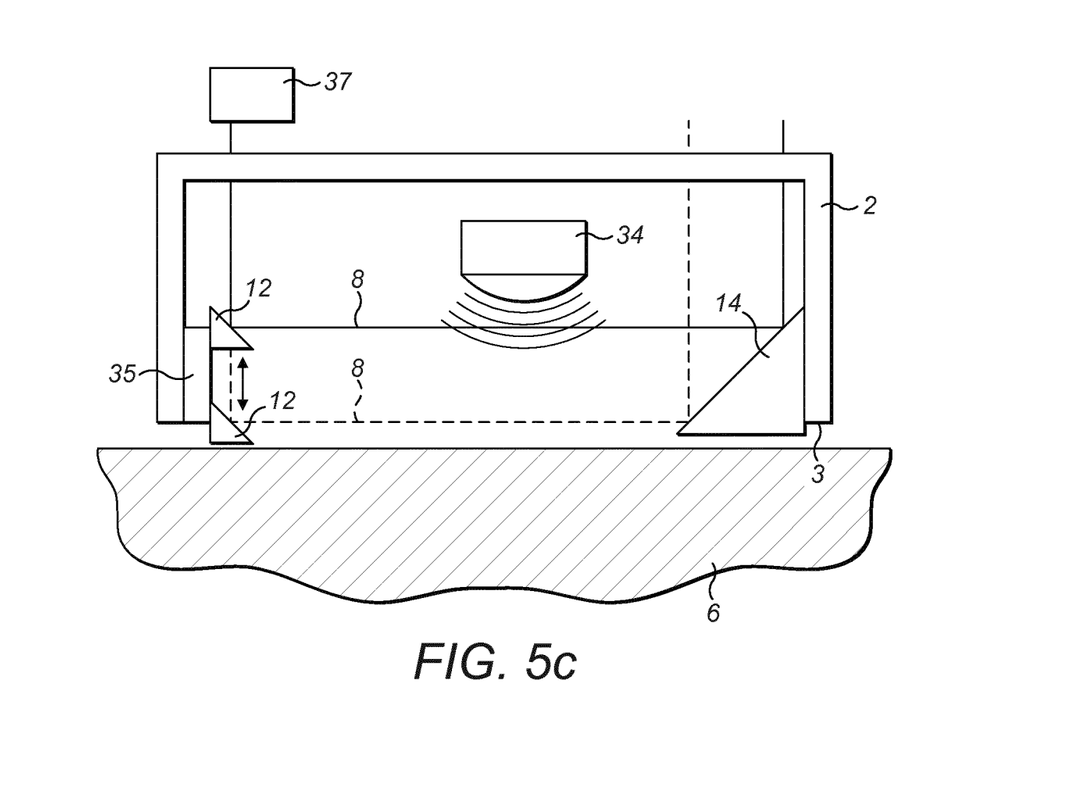
FIG. 5c shows a front view schematic diagram of another embodiment of the device for cutting hair having an optical system including an actuator.

Further embodiments of the invention are shown in FIGS. 5a to 5c. These embodiments also comprise a main body 2 having a skin contacting face 3 and an opening 4 which are pressed against the skin 6 of a user during use. However, these embodiments do not comprise a moveable frame as described with reference to FIGS. 3a to 4b. Instead, the cutting laser beam 8 is moved by an actuator 35 which is configured to move a component of the optical system, as will be explained below. Each of the embodiments shown in FIGS. 5a to 5c has a skin detector, in the form of a sensor 34, to determine the height of the skin 6 within the cutting zone 5. This skin detector sensor may comprise a displacement sensor with a sprung arm which extends to contact the skin and thereby determine its height, as described with reference to FIGS. 4a and 4b. Alternatively, as shown in FIGS. 5a and 5b, the skin detector sensor 34 may comprise an optical sensor such has a confocal lens which can measure the distance between the skin surface and a reference point on the device 2, without contacting the skin 6.

To move the cutting laser beam 8 in response to the measured height of the skin 6 in the cutting zone 5, as determined by the skin detector sensor 34, the device 1 includes a controller and an actuator 35 to move the cutting laser beam 8 by moving a component of the optical system.

The embodiment shown in FIG. 5a includes a skin detector sensor 34, in this example a confocal optical sensor, to determine the height of the skin 6 in the cutting zone 5. The device also comprises first and second reflective elements 12, 14 positioned on either side of the cutting zone 5, as described previously, to reflect an incident laser beam 13 first through 90 degrees and across the cutting zone 5 and subsequently through another 90 degrees and away towards an energy dissipater (not shown). This embodiment also includes a third reflective element 36 and an actuator 35 which is configured to move the third reflective element 36 relative to the main body 2 of the device to alter the path of the incident laser beam 13 which is incident on the first reflective element 12. For example, as shown in FIG. 5a, a laser generator 37 is disposed to emit a laser beam 38 in a direction parallel to the cutting laser beam 8 and the third reflective element 36 is disposed to reflect that laser beam 38 through 90 degrees and towards the first reflective element 12. The third reflective element 36 is configured to move, under influence of the actuator 35, either towards or away from the laser generator 37 along the path of the laser beam 38 emitted by the generator 37. In this way, the path of the incident laser beam 13 which is incident on the first reflective element 12 is moved in the direction of arrow 39, which changes the point of reflection on the first reflective element 12 and thereby adjusts the distance between the cutting laser beam 8 and the skin contacting face 3 of the main body 2.

Therefore, the distance between the skin contacting face 3 and the cutting laser beam 8 can be controlled by the controller, via the actuator 35, in response to the detected height of the skin 6 in the cutting zone 5. In this way, the effective cutting height H3 (FIG. 1b) can be adjusted in response to the determined skin height H2 (FIG. 1b) in the cutting zone 5.

The actuator 35 configured to move the third reflective element 36 of the embodiment described with reference to FIG. 5a may be a voice coil actuator or any other type of suitable controllable actuator. The third reflective element 36 may be mounted on a slide rail or guide to control the path along which it moves or the actuator 35 may have a built in guide. It will also be appreciated that the arrangement shown in FIG. 5a, with each of the reflective elements 12, 14, 36 being configured to reflect the laser beam through 90 degrees, may be altered by changing the orientation of the optical components and reflective angles of the reflective elements, without departing from the invention.

The embodiment of FIG. 5a shows an actuator 35 configured to move a third reflective element 36 along a path parallel to the cutting laser beam 8. However, it will be appreciated that an alternative embodiment of the invention would be to provide an actuator that is configured to move the laser beam generator along a path parallel to the cutting laser beam, whereby the laser beam generator emits a laser beam directly towards the first reflective element 12. In this way, the height of the cutting laser beam 8 in the cutting zone 5 is adjusted.

In another embodiment, shown in FIG. 5b, a galvanometer mirror arrangement is used to control the position of the incident laser beam 13 which is incident on the first reflective element 12, and therefore control the height of the cutting laser beam 8 in the cutting zone 5. In the example shown in FIG. 5b, the galvanometer mirror arrangement comprises two mirrors 43, 40 which are independently rotatable about parallel axes by means of at least one actuator 35, such that the direction of the incident laser beam 13 is controllable by altering the rotational positions of the two mirror 43, 40. A laser beam 41 from a laser generator 37 is incident on the first rotatable mirror 43 which reflects the laser beam towards the second rotational mirror 40 which in turn reflects the incident laser beam 13 towards the first reflective element 12 and subsequently into the cutting zone 5. In this way, by controlling the rotational position of the mirrors 43, 40 in response to a change in the detected height of the skin 6 in the cutting zone 5, as determined by the sensor 34, the incident laser beam 13 which is incident on the first reflective element 12 can be moved in the direction of arrow 42 along a direction perpendicular to its longitudinal axis, thereby controlling the height of the cutting laser beam 8 in the cutting zone 5.

It will be appreciated that other optomechatronic mechanisms may be used in place of the galvanometer mirror arrangement to control the position of the cutting laser beam 8 in the cutting zone 5.

In another embodiment, shown in FIG. 5c, the first reflective element 12, which is positioned to one side of the cutting zone 5, is mounted on an actuator 35 configured to move the first reflective element 12 towards or away from the skin contacting face 3 of the main body 2 along the path of the incident laser beam 13. In this way, the cutting laser beam 8 in the cutting zone 5 is moved to control the effective cutting height H3.

Similarly to the embodiments described with reference to FIGS. 5a and 5b, the device will comprise a skin detector, in the form of a sensor 34, to determine the height of the skin 6 in the cutting zone 5 and this sensor 34 may be the same as any of the previously described sensors. The actuator 35 may be a voice coil type actuator which is configured to move the first reflective element 12 in a linear direction along the same path as the incident laser beam 13 from a laser generator 37 such that the incident angle is not altered. The first reflective element 12 is configured to reflect the incident laser beam 13 at a right angle, across the cutting zone 5, such that it is parallel to the skin contacting face 3 of the main body 2. In this way, as the first reflective element 12 is moved along the path of the incident laser beam 13 the reflected cutting laser beam 8 in the cutting zone 5 is moved to alter the height of the cutting laser beam 8 in the cutting zone 5 and thereby adjust the effective cutting height H3. The second reflective element 14 may be mounted on a separate actuator or connected to the actuator 35 of the first reflective element 12 such that both move synchronously. Alternatively, as shown in FIG. 5c, the second reflective element 14 may be fixed, in this case the second reflective element 14 should extend far enough to ensure that the cutting laser beam 8 from the cutting zone 5 is incident on the second reflective element 14 at any position of the first reflective element 12 and height of the cutting laser beam 8 in the cutting zone 5. For example, as shown in FIG. 5c, the first reflective element 12 is mounted on an actuator 35 that moves the first reflective element 12 along the path of the incident laser beam 13 and the second reflective element 14 is fixed and is larger, extending further than the first reflective element 12 such that even at the extreme positions of the first reflective element 12 the cutting laser beam 8 from the cutting zone 5 is still incident on the second reflective element 14.

The embodiment of FIG. 5c shows an actuator 35 configured to move the first reflective element 12 along a path parallel to the incident laser beam 13, and perpendicular to the cutting laser beam 8. However, it will be appreciated that an alternative embodiment of the invention would be to provide the first reflective element 12 with an actuator that moves the first reflective element 12 along a path parallel to the cutting laser beam 8, into the cutting zone 5. In this way, the height of the cutting laser beam 8 in the cutting zone 5 is adjusted.

The embodiments described with reference to FIGS. 3a to 5c each enable the cutting height of the cutting laser beam 8 in the cutting zone 5 to be adjusted depending on the detected height of the skin 6 within the cutting zone 5. The embodiments described with reference to FIGS. 3a to 3e employ a passive system of direct between the skin 6 and a sprung frame 16 to react to changes in skin height H2. Contrastingly, the embodiments described with reference to FIGS. 4a to 5c include a skin detector sensor 32, 34, controller and actuator 31, 35 to create a closed loop control system that electronically measures changes in skin height H2 and the actuator reacts accordingly. These embodiments of the invention allow the device for cutting hair to maintain a close and uniform effective cutting height H3 without risking skin irritation as the device is moved over contours in the skin and when skin domes in the cutting zone.

It will be appreciated that any of the embodiments described with reference to FIGS. 4a to 5c, that include an actuator to control the position of the cutting laser beam, may be used to vary the cutting height of the device to alter the function of the device, rather than or as well as in reaction to variations in skin height H2. For example, for a trimming function rather than shaving of hair. The controller may include a setting for trimming hair in which case the actuator will move the laser beam further from the skin surface to provide a greater effective cutting height H3 suitable for trimming. In this case, the invention gives increased uniformity to the cut hair length which is advantageous for hair trimming devices.

All of the embodiments described enable the cutting height of the laser beam within the cutting zone to be altered relative to the skin contacting face and opening of the main body which contacts the skin. In this way, the shaver can follow contours and doming in the skin while maintaining a uniform and safe effective cutting height without the need for a lamella. This means that the skin is able to naturally deform and dome as the device is moved across the skin without risking skin irritation or poor cutting effectiveness. The movement of the cutting beam means that the function of the lamella to press the skin down flat in the cutting zone is not required. The open end of the cutting zone is preferable because it allows hair to freely enter the cutting zone and reduces accumulation of debris around the cutting zone.

However, it will be appreciated that the movement of the cutting beam in reaction to changes in the skin height within the cutting zone does not preclude use of a lamella. On the contrary, the adjustment mechanism may allow the use of a thinner and more lightweight lamella with larger apertures, thereby overcoming many of the disadvantages of using a lamella, without risking overt laser-skin interaction or reduced cutting effectiveness. A thin, lightweight lamella with large apertures that possibly only extends partially across the opening of the cutting zone will reduce doming and reduce the amount of movement required for the cutting laser beam, although some movement will always be advantageous.

Moreover, the cutting height adjustment may be employed with a full, conventional lamella, with the height adjustment mechanism being used to change the cutting height of the device between a trimming function (increased cutting height for uniform remaining hair length) and a shaving function (close shave). In this case, any sensor should be configured to measure the distance between the laser beam and the lamella, rather than between the laser beam and the skin surface.

In the embodiments described with reference to FIGS. 1a to 5c, the second reflective element is configured to reflect the laser beam from the cutting zone towards an energy dissipater which dissipates the laser beam and prevents any further damage being caused by the laser beam. However, it will be appreciated that the second reflective element may instead be configured to reflect the laser beam back across the cutting zone, parallel to and spaced from the first laser beam in the cutting zone and thereby create a multi-beam cutting action. This may be repeated multiple times. In this case, all of the reflective elements may be required to move in the same manner as described with reference to the embodiments shown in FIGS. 3a to 5c. A subsequent reflective element may reflect the laser beam towards an energy dissipater after the laser beam has passed across the cutting zone a number of times.

Although each of the embodiments of the invention described move the laser beam in such a way as the laser beam remains parallel to the skin contacting face of the device, it will be appreciated that the moveable frame, actuator and/or optical system may be configured to move the laser beam in such a way that it does not remain parallel to the skin contacting face of the device. For example, the frame may be able to rotate as well as slide in response to changes in the height of the skin in the cutting zone. Alternatively, the optical system may be provided with an optomechatronic system that acts in response to multiple skin height sensors positioned across the cutting zone to change the height and angle of the laser beam.

It will be appreciated that the term "comprising" does not exclude other elements or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A device for cutting hair comprising:
   a skin contacting face configured to be placed against a surface of the skin of a user during use;
   an optical system configured to direct a cutting laser beam across a cutting zone, the cutting laser beam being directed parallel to and spaced from the skin contacting face to cut hairs extending into the cutting zone; and
   a laser positioning mechanism configured to change a distance between the cutting laser beam and the skin contacting face to maintain a predetermined distance between the cutting laser beam and the surface of the skin of the user when the device is in use.

2. The device of claim 1, wherein the optical system includes at least a first reflective element, configured to reflect an incident laser beam to provide the cutting laser beam across the cutting zone, and wherein the laser positioning mechanism comprises an actuator configured to move at least the first reflective element to adjust the distance between the cutting laser beam and the skin contacting face of the device.

3. The device of claim 2, wherein the actuator is configured to move the first reflective element either along a path of the incident laser beam or along a path of the cutting laser beam in the cutting zone.

4. The device of claim 2, wherein the optical system comprises an additional reflective element, configured to reflect an emitted laser beam, emitted from a laser generator, to provide the incident laser beam such that the incident laser beam is incident on the first reflective element, and wherein the actuator is configured to move the additional reflective element to adjust the path of the incident laser beam and thereby adjust the distance between the cutting laser beam and the skin contacting face.

5. The device of claim 2, wherein the optical system further comprises two rotational reflective elements rotatably mounted on parallel axes, wherein the two rotational reflective elements are configured to reflect an emitter laser beam onto the first reflective element, and where the actuator is configured to rotate the two rotational reflective elements to adjust the path of the incident laser beam which is incident on the first reflective element.

6. The device of claim 1, wherein the laser positioning mechanism comprises an electronic sensor arranged to detect the surface of the skin in the cutting zone and an actuator configured to move the laser positioning mechanism to maintain the predetermined distance between the cutting laser beam and the surface of the skin of the user when the device is in use.

7. A device for cutting hair compromising:
a skin contacting face configured to be placed against a surface of the skin of a user during use;
an optical system configured to direct a cutting laser beam across a cutting zone, so that the cutting laser beam is parallel to and spaced from the skin contacting face to cut hairs extending into the cutting zone; and
a laser positioning mechanism configured to change a distance between the cutting laser beam and the skin contacting face to maintain a predetermined distance between the cutting laser beam and the surface of the skin of the user when the device is in use,
wherein the laser positioning mechanism comprises a skin surface follower attached to the optical system, the skin surface follower being arranged so that, when the device is in use, the skin surface follower contacts the surface of the skin below the cutting laser beam so that the skin surface follower moves together with the optical system relative to the skin contacting face to change the distance between the cutting laser beam and the skin contacting face.

8. The device of claim 7, wherein the skin surface follower is configured to contact the surface of the skin of the user in a vicinity of the cutting laser beam in the cutting zone when the device is in use.

9. The device of claim 7, wherein the laser positioning mechanism comprises a frame which is moveably mounted within the device, the frame comprising the skin surface follower and the optical system.

10. The device of claim 9, further comprising a spring element to bias the moveable frame in a direction towards the surface of the skin so that the skin surface follower remains in contact with the surface of the skin when the device is in use.

11. The device of claim 9, wherein the optical system comprises a first reflective element positioned to reflect an incident laser beam across the cutting zone.

12. The device of claim 11, wherein the skin surface follower comprises a distal face that forms the first reflective element.

13. The device of claim 7, wherein the skin surface follower comprises an aperture and the cutting laser beam extends across the cutting zone and through the aperture.

14. The device of claim 7, wherein the skin surface follower comprises a recess and the cutting laser beam extends across the cutting zone within the recess.

15. A device for cutting hair comprising:
a skin contacting face configured to be placed against a surface of the skin of a user during use;
an optical system configured to direct a cutting laser beam across a cutting zone, so that the cutting laser beam is parallel to and spaced from the skin contacting face to cut hairs extending into the cutting zone; and
a laser positioning mechanism configured to change a distance between the cutting laser beam and the skin contacting face to maintain a predetermined distance between the cutting laser beam and the surface of the skin of the user when the device is in use,
wherein the laser positioning mechanism comprises a frame moveably mounted within the device and on which is mounted the optical system, wherein the frame is movable by an actuator to maintain the predetermined distance between the cutting laser beam and the surface of the skin of the user when the device is in use.

* * * * *